(12) United States Patent
Naveca et al.

(10) Patent No.: US 12,313,555 B2
(45) Date of Patent: May 27, 2025

(54) LAMP ASSAY DEVICE

(71) Applicant: FUNDAÇÃO OSWALDO CRUZ, Manguinhos (BR)

(72) Inventors: Felipe Gomes Naveca, Manaus (BR); Valdinete Alves Do Nascimento, Manaus (BR); Victor Costa De Souza, Manaus (BR); Dana Cristina Da Silva Monteiro, Manaus (BR); Arlesson Viana Da Silva, Rio Grande (BR); Carlos Raimundo Pereira Dos Santos Junior, Manaus (BR); Thiago Daniel De O. Moura, Contagem (BR); Valtemar Fernandes Cardoso, Adrianópolis (BR)

(73) Assignee: FUNDAÇÃO OSWALDO CRUZ, Manguinhos (BR)

( * ) Notice: Subject to any disclaimer, the term of this patent is extended or adjusted under 35 U.S.C. 154(b) by 1005 days.

(21) Appl. No.: 16/968,354

(22) PCT Filed: Feb. 7, 2019

(86) PCT No.: PCT/BR2019/050032
§ 371 (c)(1),
(2) Date: Aug. 7, 2020

(87) PCT Pub. No.: WO2019/153061
PCT Pub. Date: Aug. 15, 2019

(65) Prior Publication Data
US 2021/0190698 A1 Jun. 24, 2021

(30) Foreign Application Priority Data
Feb. 7, 2018 (BR) ...................... BR1020180025759

(51) Int. Cl.
G01N 21/78 (2006.01)
B01L 7/00 (2006.01)
C12Q 1/6844 (2018.01)

(52) U.S. Cl.
CPC ................ *G01N 21/78* (2013.01); *B01L 7/00* (2013.01); *C12Q 1/6844* (2013.01); *B01L 2300/0645* (2013.01); *B01L 2300/0663* (2013.01)

(58) Field of Classification Search
CPC ......... G01N 21/78; C12Q 1/6844; B01L 7/00; B01L 2300/0645; B01L 2300/0663
See application file for complete search history.

(56) References Cited

U.S. PATENT DOCUMENTS 9,476,836 B2 10/2016 Miyamoto et al.
2013/0331298 A1 12/2013 Rea
(Continued)

FOREIGN PATENT DOCUMENTS

CN 101405410 A * 4/2009 ............ B01L 3/5027
CN 104498353 4/2015
(Continued)

OTHER PUBLICATIONS

Espacenet English Machine Translation of CN 101405410. (Year: 2009).*
(Continued)

*Primary Examiner* — Kathryn Elizabeth Limbaugh

(57) ABSTRACT

The present invention provides a LAMP assay device comprising a heating chamber (5) adapted to receive a support rail (2) of at least one sample, in which the support rail (2) is inserted into it through a sample insertion opening (1), in addition, the heating chamber (5) comprises: at least one internal heating element (8a, 8b); a circuit of light-emitting elements (6) positioned on a front or rear wall; and a light (Continued)

sensor circuit (7) on a wall opposite the light emitting element circuit (6).

18 Claims, 3 Drawing Sheets

(56) References Cited

U.S. PATENT DOCUMENTS

| | | |
|---|---|---|
| 2014/0349298 A1 | 11/2014 | Stanchina et al. |
| 2014/0356874 A1 | 12/2014 | Bearinger et al. |
| 2016/0231324 A1 | 8/2016 | Zhao et al. |

FOREIGN PATENT DOCUMENTS

| | | | |
|---|---|---|---|
| CN | 106442493 A | * | 2/2017 |
| WO | WO 2011/150115 | | 12/2011 |
| WO | WO 2013/043203 | | 3/2013 |
| WO | WO-2017025984 A1 | * | 2/2017 |

OTHER PUBLICATIONS

Espacenet English Machine Translation of CN 106442493. (Year: 2017).*

Corte, "Control System for Thermocycler," 2016, Dissertation (Masters) [online]—Electrical Engineering Course, Polytechnic School, University of Vale do Rio dos Sinos, Sao Leopoldo, Accessed on: Apr. 25, 2019, available at: <http://www.repositorio.jesuita.org.br/handle/UNISINOS/5998> [In Portuguese, machine translation attached; cited by the ISR and Written Opinion].

International Search Report issued May 6, 2019, in PCT/BR2019/050032, including translation.

Ahmed et al., "Development and evaluation of real-time loop-mediated isothermal amplification assay for rapid detection of cystic echinococcosis," BMC Veterinary Research, 2016, 12:202, 10 pp.

Sayad et al., "A microfluidic lab-on-a-disc integrated loop mediated isothermal amplification for foodborne pathogen detection," Sensors and Actuators, 2016, 227:600-609.

Wang et al., "A novel CMOS image sensor system for quantitative loop-mediated isothermal amplification assays to detect food-borne pathogens," Journal of Microbiological Methods, 2017, 133:1-7.

* cited by examiner

LAMP ASSAY DEVICE

FIELD OF INVENTION

The present invention is related to assay techniques known as LAMP, from the English "Loop Mediated Isothermal Amplification". More particularly, the invention relates to a LAMP assay device, which aims to amplify the DNA/cDNA for detecting the genetic material of pathogens extracted from a biological sample.

BACKGROUND OF THE INVENTION

Loop-mediated isothermal DNA amplification techniques, also known as LAMP (Loop-Mediated Isothermal Amplification) techniques, are widely known in the status of technique, and applied to the development of diagnostic tests for the detection of parasites in biological samples.

The LAMP technique is increasingly used to replace the PCR technique (Polymerase Chain Reaction-Polymerase Chain Reaction), since the time and cost to perform the PCR technique still make it impossible to use it on a large scale in routine laboratories.

The LAMP assays are performed in isothermal conditions, which can be maintained in different instruments, such as thermocyclers and water baths, or else LAMP assay devices as adopted in this report. This equipment makes it possible to amplify the DNA/cDNA of samples to detect pathogens by heating an assay chamber inside the device.

In the assays developed on the equipment referred to in this report, in summary form, aliquots of a biological sample under analysis are added to the reagents and the set is heated in a LAMP assay chamber. These samples are then monitored during the assay in order to identify a possible color change (for example, from violet to sky blue when using the hydroxynaphthol blue reagent), which represents a positive reaction of the sample with respect to the reagent used.

Various configurations of LAMP assay chambers are known from the status of technique, which will be described in the following paragraphs.

The article "*A novel CMOS image sensor system for quantitative loop-mediated isothermal amplification assays to detect food-borne pathogens*", by Wang, T T, published in "*Journal of microbiological methods*", presents a low-cost CMOS image sensor system for LAMP assays to detect food-borne pathogens. The described system monitors the photon variation, caused by color changes during amplification, in real time. The article concludes by stating that the simple, compact and low-cost design, with low energy consumption, represents a significant advance in the development of portable, sensitive, easy-to-use, real-time quantitative analytical tools for on-site diagnosis.

The article "*Development and evaluation of real-time loop-mediated isothermal amplification assay for rapid detection of cystic echinococcosis*", by Ahmed, M E, published in "*BMC Veterinary Research*", describes the development and evaluation of a real-time LAMP assay for rapid detection of cystic echinococcosis. The described assay was carried out at a constant temperature (63° C.), with real-time monitoring using an amplification and detection instrument and fluorochrome dye. After amplification cycles in a water bath, LAMP products were observed to detect color changes with the naked eye and were visualized under a UV light source.

The article "*A microfluidic lab-on-a-disc integrated loop mediated isothermal amplification for foodborne pathogen detection*" by Sayad, A A, published in "*Sensors And Actuators B-Chemical*" reports a LAMP amplification centrifugal microfluidic device for detection of food pathogens, in which a source of forced convection heating was used to actuate a wax valve and temperature heating for LAMP amplification.

The document WO2013043203 is directed to a container for LAMP assays of isothermal and non-isothermal nucleic acids comprising a body having an inner/outer surface and an open end, in addition to a plug-in lid with the open end of the body and flexible material extending through of the passage.

According to this document, the developed container guarantees greater flexibility compared to the known microfluidic chips due to its inherent flexibility for handling small and large volumes of fluids. Another outstanding advantage would be the fact that the revealed container can also allow the extraction of samples, and have fluid transfer functionalities.

The document US20160231324 describes a high performance multiplexing system for detecting a target that comprises encapsulating a biological sample with an assay or sensor comprising, for example, DNA enzyme capable of generating a detectable signal and detecting the signal, in which the assay system, or sensor, comprises an assay based on LAMP.

According to this document, the analyzed sample can be heated, in which the system would comprise a light emitting diode and a detector, in addition to data analysis software, visual displays to transmit information, connections with electronic devices, among other characteristics.

The document WO2011150115 is directed to a LAMP method and a device for the in situ detection of nucleic acid in a sample. It is described that the method used comprises the introduction of nucleic acid amplification reagents and heating of the nucleic acid amplification reagents.

According to this document, the heating step is performed using a disposable heater, and the detection step involves the detection of a color change in a colorimetric dye in fluid communication with the nucleic acid amplification reagents. Little constructive detail about the described device is provided.

The document US20140356874 discloses a method and device for portable nucleic acid amplification and detection in which the instrument preferably uses an isothermal nucleic acid amplification technique, such as LAMP. Detection of the target amplification can be achieved, for example, by detecting a color shift or fluorescence in a dye added to the amplification reaction.

According to this document, the disclosed device comprises a heating chamber, in which the sample is heated and a sensor to detect the color change of the sample, where the elements can be controlled by a central control system.

The document U.S. Pat. No. 9,476,836 discloses a method for detecting nucleic acid (DNA) by the LAMP method in a sample (for example, Blood) which involves bringing the nucleic acid into contact with a detection reagent inside a closed system, and observing the color change of nucleic acid and/or detection reagent.

It is further described that the observation of the color change under visible light can also be performed by measuring the absorbance of the sample solution in the visible light range.

However, little information is provided regarding the construction details of the device as a whole, such as the arrangement of sensors and light sources, display devices, etc.

The document US20130331298 discloses an assay cartridge for detecting a variety of analytes, including pathogens, comprising an injection port, a central channel, processing chambers, reagent containers and a waste chamber. It is described that the assay in question may be of the LAMP type.

The described device further comprises a series of elements, such as heater, heater controller, optical sensors for measuring the flow flowing in the cartridge. Nothing is said about the use of sensors to identify a color change in the sample under analysis.

Therefore, in the light of the aforementioned documents, it is noted that the status of technique comprises a series of equipment for reacting and reading LAMP assays, with different configurations, in which many improvements can still be proposed, especially with regard to practicality and effectiveness in carrying out LAMP assays in loco.

Thus, as it will be more detailed in the next sections, the present invention aims at presenting a LAMP assay chamber that comprises constructive characteristics that facilitate its use and make the assays more efficient.

SUMMARY OF THE INVENTION

The present invention aims to provide a device for LAMP assays that allows the performance of LAMP assays efficiently, simply and quickly.

In order to achieve the objectives described above, the present invention provides a LAMP assay device comprising a heating chamber adapted to receive a support rail of at least one sample, in which the support rail is inserted into it through a sample insertion opening, in addition, the heating chamber comprises: at least one internal heating element, with a microcontrolled temperature circuit; a circuit of light-emitting elements positioned on a front or rear wall; and a circuit of light sensors on a wall opposite the circuit of light-emitting elements.

BRIEF DESCRIPTION OF THE FIGURES

This detailed description makes reference to the attached figures and their respective reference numbers.

DETAILED DESCRIPTION OF THE INVENTION

Preliminarily, it is emphasized that the description that follows will start from a preferred embodiment of the invention. As will be clear to any person skilled in the subject, however, the invention is not limited to that particular embodiment.

As previously mentioned, the objective of the present invention is to provide a low cost and practical use LAMP assay device. Thus, the LAMP assay device described below aims to amplify the DNA/cDNA to detect diseases by heating a resistive system, where the control performed is based on the thermal inertia of the resistive elements allocated inside the device.

The LAMP assay device, in general, comprises integrated circuits directly in its structure that allow the realization of the thermal control and detection of the color change of the samples. The detection set consists of light emitters and detectors that monitor the color change of the samples evaluated during the assay, recording the moment when the color change occurs in the case of a positive reaction.

The main cost reduction and differential of this device is the exclusive use of thermal inertia for temperature control, which differs from the invention of commercial systems that use removal and/or cooling techniques to control temperature, increasing equipment costs, as well as your energy consumption.

The advantages described above will be more evident from the description of the figures that follows.

Figure 1:
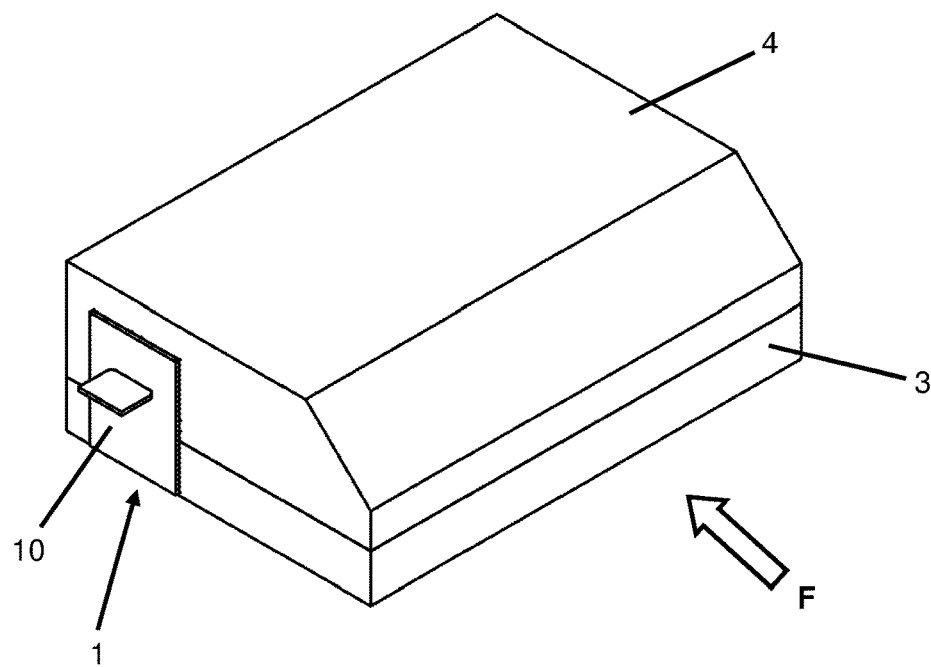
FIG. 1 illustrates a perspective view of an optional configuration of the LAMP assay device of the present invention.

FIG. 1 illustrates a perspective view of an optional configuration of the LAMP assay device of the present invention. It is observed that the LAMP assay device comprises a sample insertion opening 1, preferably positioned on a side wall of the device.

Figure 2:
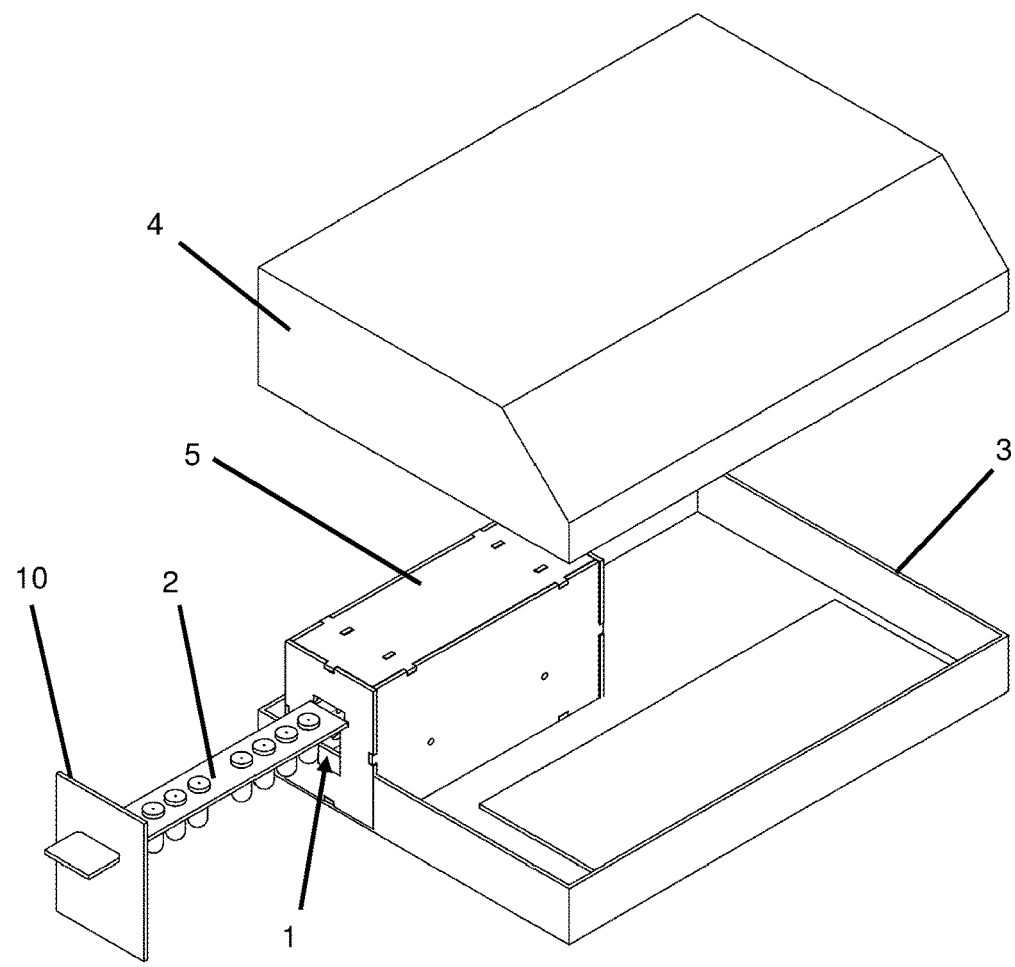
FIG. 2 illustrates a disassembled view of the LAMP assay device shown in FIG. 1.

FIG. 2 shows a disassembled view of the LAMP assay device shown in FIG. 1. In this optional configuration, the device comprises a base 3, an upper cover 4 and a support rail 2 of at least one sample. In order to facilitate the description, the support rail 2 of at least one sample will be referred to simply as the support rail 2.

The device further comprises a heating chamber 5, in which the support rail 2 is inserted into it through the sample insertion opening 1. In addition, at least one integrated circuit board can be attached directly to the base frame 3.

The integrated circuit is adapted to perform the thermal control and the detection of the color change of the samples, as will be more detailed later in this report.

Optionally, at least one integrated circuit can be attached to the top cover 4 of the device. Other elements, such as trigger buttons, informational displays, among others, can also be positioned on the top cover 4 of the device.

Figure 3:
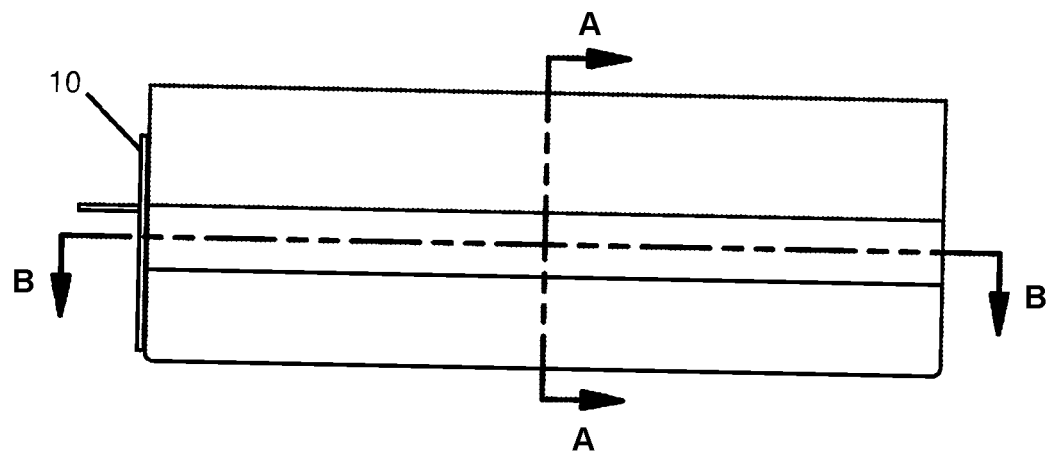
FIG. 3 illustrates a front view of the optional configuration of the LAMP assay device shown in FIG. 1.

FIG. 3 shows a front view of the optional configuration of the LAMP assay device shown in FIG. 1.

Figure 4:
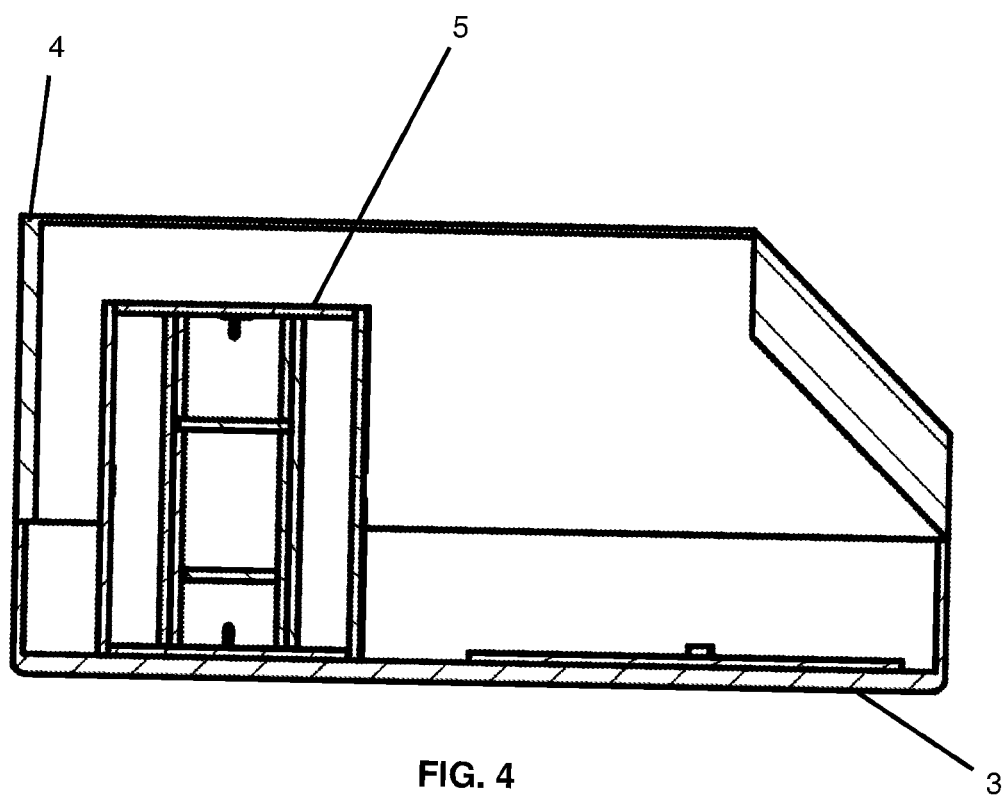
FIG. 4 illustrates the section AA shown in FIG. 3.
Figure 5:
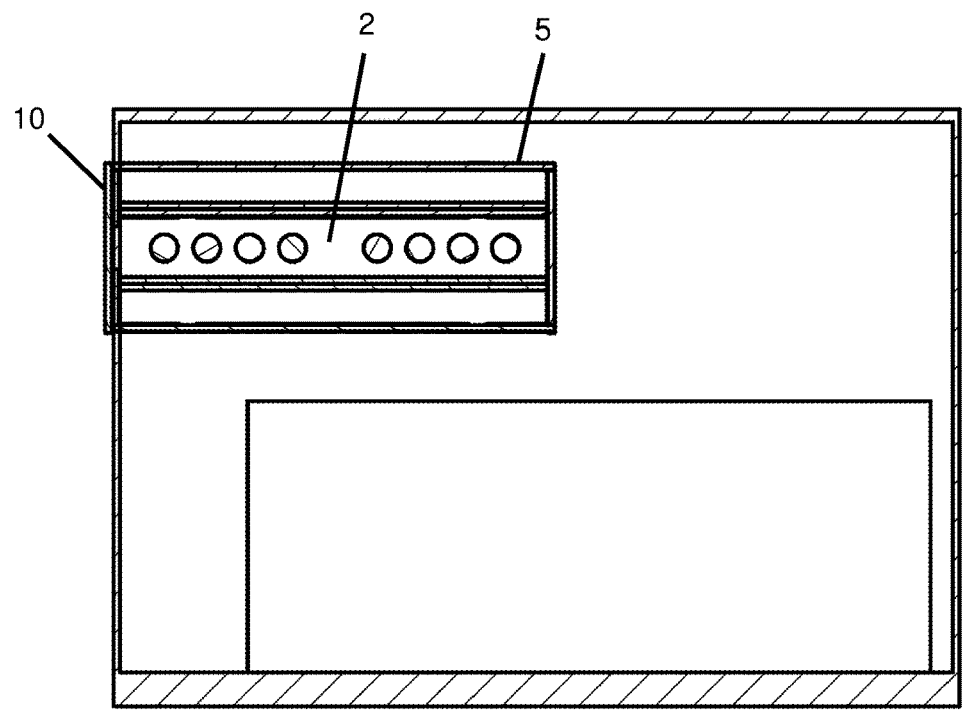
FIG. 5 illustrates the BB section shown in FIG. 3.

FIG. 4 shows the section AA shown in FIG. 3, and FIG. 5 shows the section BB shown in FIG. 3.

It is observed more clearly that the heating chamber 5 is adapted to receive the support rail 2 of at least one sample of biological material inside it.

Optionally, the support rail 2 comprises a side wall 10 at its outer end. In this way, when the rail is completely inserted in the heating chamber 5, the side wall 10 provides the insulation of the inner region of the heating chamber 5.

It is important to note that the number of samples that the support rail 2 can accommodate is variable according to each embodiment. The minimum number provided is one sample, however, as many samples may be accommodated as necessary in specific embodiments.

Figure 6:
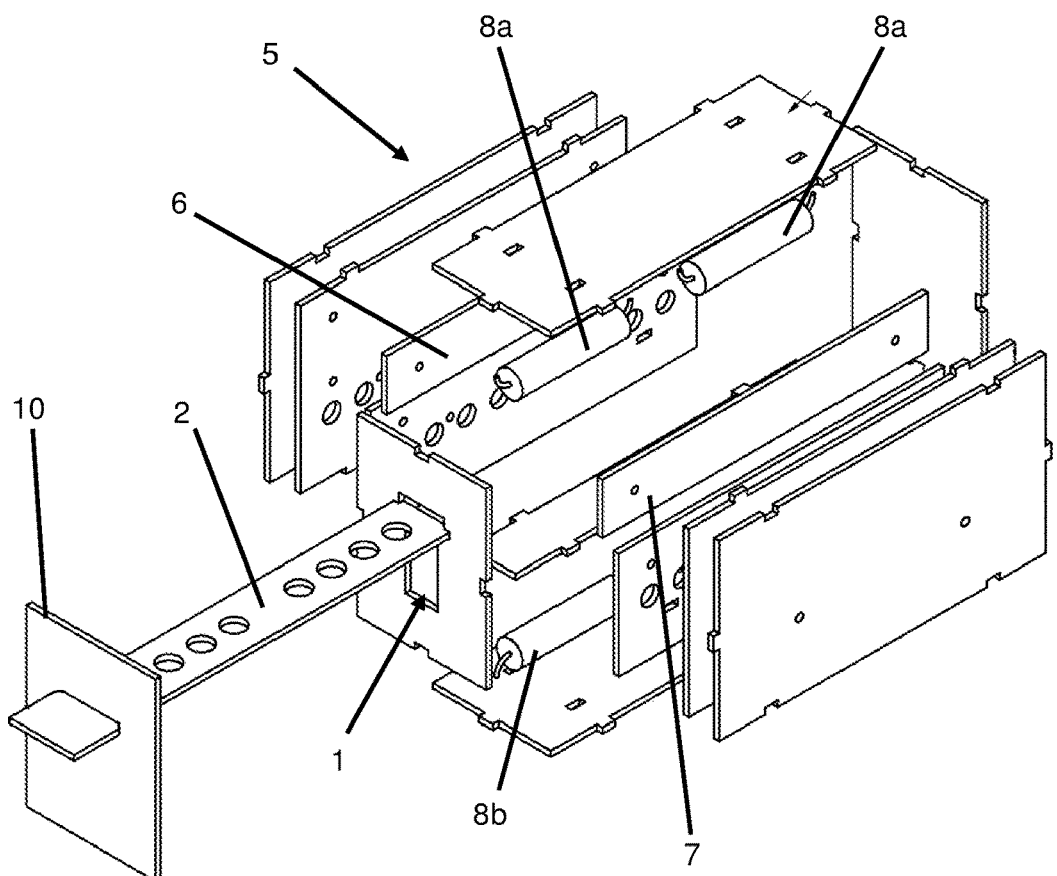
FIG. 6 illustrates an isolated and exploded view of the heating chamber according to an optional configuration of the present invention.

FIG. 6 illustrates an isolated and exploded view of the heating chamber 5 according to an optional configuration of the present invention. The heating chamber 5 comprises at least one internal heating element 8a, 8b. The at least one heating element 8a, 8b is adapted to heat the interior of the heating chamber 5, which can provide for the initiation of the reaction in the samples, as previously described.

Optionally, at least two heating elements are positioned inside the heating chamber 5, where at least one lower heating element 8b is positioned in a lower portion of the heating chamber 5, and at least one upper heating element 8a is positioned in an upper portion of the heating chamber 5. In the example illustrated in FIG. 6, two heating elements are positioned in the upper portion of the chamber and two in the lower portion, however, it is emphasized that this configuration is optional.

When the configuration described in the previous paragraph is adopted, the upper heating element 8a produces greater calorific value, configured through the microcontrolled circuit. In turn, the lower heating element 8b comprises a heating circuit with less calorific value, resulting from the configuration of the microcontrolled circuit. This configuration is adopted in order to obtain less thermal radiation at the bottom of the heating chamber 5, thereby preventing the evaporation of the most volatile compounds from the microtubes during the assay.

It is also provided that the heating chamber 5 comprises a circuit of light-emitting elements 6, preferably light-emitting diodes 6 (LED), positioned on the front or rear wall.

Positioned in the heating chamber 5 in a position opposite to the circuit of light emitting elements 6, a circuit of light sensors 7 is also provided, optionally LDRs (Light Dependent Resistors).

Preferably, a light-emitting element and a light-sensing element are positioned at opposite points with respect to each sample inside the chamber. In this way, the circuit of light emitting elements 6 illuminates the samples inside the heating chamber 5 and the circuit of light sensors 7 identifies the color of the light emitted by each sample.

This system must be controlled by a real-time control system, in order to identify the exact moment when a sample undergoes any color change.

In order to control the temperature inside the heating chamber 5, it is also optionally provided that the heating chamber 5 comprises a temperature sensor positioned inside it. The temperature sensor is preferably positioned in an intermediate region of the heating chamber 5.

The temperature sensor must also be in communication with a control system. Thus, the control system will manage the power of at least one heating element 8a, 8b in response to the information received by the temperature sensors, keeping the heating chamber 5 at the desired and planned temperature for each assay.

Preferably, the control system is positioned on an upper wall of the heating chamber 5 and is in communication with the other elements described, namely, at least one heating element 8a, 8b, the circuit of light emitting elements 6, the light sensor circuit 7 and the temperature sensor. In addition, the control system can control power supply for all of these elements.

Thus, the control system acts as a processing, control and communication unit of the heating chamber 5.

In summary, according to the previously described, the detection set consists of light emitters 6 and detectors that monitor the color change of the samples evaluated during the assay, recording the moment when the color change occurs, in this case of a positive reaction.

It is important to note that the polarization of the resistive elements, internal to the assay chamber, causes the current flow that generates heat through the power dissipation, a phenomenon known as the Joule effect, applied in this case to obtain a homogeneous temperature range in the region where the samples are positioned for reaction.

Thus, the heating chamber 5 has the objective of low cost and in this case no form of heat and/or circulation removal is applied, in order to obtain thermal homogeneity only by controlling the current flow through the element resistive considering its thermal inertia to maintain the internal environment of the chamber in the temperature range determined for reaction.

Therefore, after preheating, the system operates through a dedicated control that adjusts the heat capacity necessary for the temperature balance inside the heating chamber 5. This control is done by the control system, through the information of the sensor elements distributed in the region of the samples correlating the thermal inertia of the heating element 8a, 8b so that there are no variations outside the sample reaction range.

The current flow applied to the heating element 8a, 8b needs to be aligned with the thermal inertia of the heating element 8a, 8b due to the time it takes to deliver the amount of heat necessary to reach the equilibrium temperature determined for the assay.

In this way, the system works by measuring the speed with which the environment inside the chamber gains or loses heat to the external environment and creates a controlled compensation for the current flow applied to the heating element 8a, 8b. Since the thermal inertia of the air is not high, long periods of thermal equilibrium are not necessary. In addition, the good thermal conductivity of the air also helps to homogenize the temperature inside the chamber.

Therefore, the ability of the LAMP assay device described to change the temperature quickly is given by the thermal inertia that is directly related to the thermal constant, heat capacity and the mass to be heated inside the heating chamber 5. The purpose of thermal control is to regulate the established temperature limits, within the time determined for each reaction, so that the system acts safely.

Optionally, the top cover 4 of the LAMP assay device can comprise trigger and configuration buttons, a visualization display, and other interface elements as deemed necessary. These interface elements are intended to make it possible to configure and control the device in each application.

It should be noted that all interface elements must be in communication with the control system described above.

Optionally, the management of the buttons, the collection of data from the sensors, the display of messages on the display and the temperature control of the chamber are performed by a program written in C language, called embedded software.

Also optionally, the LAMP assay device can comprise a means to remotely connect to electronic devices that allow to control and/or view the assays performed, download assays data/results, among other functions. This connection can be made wirelessly or using cables.

The operating mode of the LAMP assay device may be as described below.

Initially, the device is connected to a power supply source and an On/Off switch is activated. Before starting the reaction mode, the sample support rail 2 must be kept outside the heating chamber 5.

Using the user interface (buttons), the system is started, entering a stabilization cycle for a predetermined period of time to reach the temperature range determined for the assay to be performed. At this time, the display may show a message indicating that the camera is being stabilized.

After the time required for temperature stabilization has elapsed, the system will be ready to start the reaction assay and a message may be displayed, indicating that the heating chamber 5 is stabilized.

After the stabilization cycle, that is, with the temperature suitable for the assay stabilized inside the heating chamber 5, the sample support rail 2 is inserted into the heating chamber 5 through the sample insertion opening 1. At that moment, the command to start the reaction is given. The reaction start command can be given via a button on the top cover 4 of the device or any other means, such as remote control.

During the reaction assay, the internal temperature information of the chamber, the elapsed time of the assay, the color reading value of each sample, as well as any other information deemed relevant are shown on the display.

After the determined assay time for the reaction has elapsed, the assay is ended and the display may show a message stating: the assay result; user instructions; or other relevant information.

It is noteworthy that the control system of the LAMP assay device can also connect remotely, via remote connection technology Bluetooth® technology, to other electronic devices (such as computers, smartphones, notebooks, etc.) in order to produce tables, graphs, data plotting assays, and export any relevant information from the assays performed.

Thus, it is clear that the proposed LAMP assay device solves the status of technique problems it proposes, that is, it allows the performance of LAMP assays efficiently, simply and quickly.

A wide range of variations on the scope of protection of this application are allowed. Consequently, it is reinforced that this invention is not limited to the particular settings/embodiments described above.

The invention claimed is:

1. A loop-mediated isothermal amplification (LAMP) assay device comprising:
   a heating chamber wherein the heating chamber comprises:
      at least one internal heating element fixed inside the heating chamber;
      a circuit of light-emitting elements positioned on one of a front wall or a rear wall of the heating chamber; and
      a circuit of light sensors positioned opposite the circuit of light-emitting elements on one of the front wall or the rear wall of the heating chamber;
   a removeable support rail wherein the heating chamber is configured to receive the removeable support rail configured to hold one or more samples when the removeable support rail is inserted into the heating chamber through a sample insertion opening; and
   a real-time control system wherein the real-time control system is configured to control a temperature of the heating chamber during a stabilization cycle while the removeable support rail is outside the heating chamber by controlling current flow through the at least one internal heating element fixed inside the heating chamber, and
      wherein after the stabilization cycle, the real-time control system is configured to control a temperature of the heating chamber during a reaction mode exclusively based on thermal inertia of the at least one internal heating element of the heating chamber by controlling current flow through the at least one internal heating element fixed inside the heating chamber based on a speed with which an environment inside the heating chamber gains or loses heat to an environment outside the heating chamber while the removeable support rail is inserted into the heating chamber.

2. The device according to claim 1, wherein for each sample of the one or more samples that the heating chamber is configured to receive, one of the light-emitting elements is configured to be positioned opposite one of the light sensors.

3. The device according to claim 1, further comprising a base and an upper cover, wherein the heating chamber is positioned on the base.

4. The device according to claim 1, wherein the sample insertion opening is positioned on a side wall of the device.

5. The device according to claim 1, wherein the removeable support rail comprises a side wall at an outer end of the removeable support rail, the side wall being adapted to close the sample insertion opening.

6. The device according to claim 1,
   wherein the heating chamber comprises at least two internal heating elements, one of the internal heating elements being positioned in a lower portion of the heating chamber, and another one of the internal heating elements being positioned in an upper portion of the heating chamber,
   wherein the at least two internal heating elements are of a resistive type, and
   wherein the internal heating element positioned in the upper portion comprises a heating circuit with a first resistance value and the internal heating element positioned in the lower portion comprises a heating circuit with a second resistance value, the first resistance value being less than the second resistance value.

7. The device according to claim 1, wherein the heating chamber comprises a temperature sensor positioned inside the heating chamber.

8. The device according to claim 1, further comprising at least one of: a visualization display; a connection with electronic devices; a user interface; an electrical power source; and one or more trigger buttons.

9. The device according to claim 1, a wherein the real-time control system is in communication with at least one of: the at least one internal heating element; the circuit of light-emitting elements; the circuit of light sensors; a temperature sensor; a visualization display; electronic devices; a user interface; an electrical power source; and one or more trigger buttons.

10. The device according to claim 2, further comprising a base and an upper cover, wherein the heating chamber is positioned on the base.

11. The device according to claim 10, wherein the sample insertion opening is positioned on a side wall of the device.

12. The device according to claim 11, wherein the removeable support rail comprises a side wall at an outer end of the removeable support rail, the side wall being adapted to close the sample insertion opening.

13. The device according to claim 12,
   wherein the heating chamber comprises at least two internal heating elements, one of the internal heating elements being positioned in a lower portion of the heating chamber, and another one of the internal heating elements being positioned in an upper portion of the heating chamber,
   wherein the at least two internal heating elements are of a resistive type, and
   wherein the internal heating element positioned in the upper portion comprises a heating circuit with a first resistance value and the internal heating element positioned in the lower portion comprises a heating circuit with a second resistance value, the first resistance value being less than the second resistance value.

14. The device according to claim 13, wherein the heating chamber comprises a temperature sensor positioned inside the heating chamber.

15. The device according to claim 13, further comprising at least one of: a visualization display; a connection with electronic devices; a user interface; an electrical power source; and one or more trigger buttons.

16. The device according to claim 15, wherein the real-time control system is in communication with at least one of: the at least one internal heating element; the circuit of light-emitting elements; the circuit of light sensors; a temperature sensor; a visualization display; electronic devices; a user interface; an electrical power source; and one or more trigger buttons.

17. A loop-mediated isothermal amplification (LAMP) assay device comprising:
a heating chamber wherein the heating chamber comprises:
at least two internal heating elements;
a circuit of light-emitting elements positioned on one of a front wall or a rear wall of the heating chamber; and
a circuit of light sensors positioned opposite the circuit of light-emitting elements on one of the front wall or the rear wall of the heating chamber;
a removeable support rail wherein the heating chamber is configured to receive the removeable support rail configured to hold one or more samples when the removeable support rail is inserted into the heating chamber through a sample insertion opening; and
a real-time control system wherein the real-time control system is configured to control a temperature of the heating chamber during a stabilization cycle while the removeable support rail is outside the heating chamber by controlling current flow through the at least two internal heating elements fixed inside the heating chamber,
wherein after the stabilization cycle, the real-time control system is configured to provide thermal control exclusively based on thermal inertia of the at least two internal heating elements of the heating chamber during a reaction mode based on a speed with which an environment inside the heating chamber gains or loses heat to an environment outside the heating chamber while the removeable support rail is inserted into the heating chamber,
wherein for each sample of the one or more samples that the removeable support rail is configured to hold, one of the light-emitting elements is configured to be positioned opposite one of the light sensors,
wherein one of the internal heating elements is positioned in a lower portion of the heating chamber, and another one of the internal heating elements is positioned in an upper portion of the heating chamber,
wherein the at least two internal heating elements are of a resistive type and are fixed inside the heating chamber, and
wherein the internal heating element positioned in the upper portion comprises a heating circuit with a first resistance value and the internal heating element positioned in the lower portion comprises a heating circuit with a second resistance value, the first resistance value being less than the second resistance value.

18. A loop-mediated isothermal amplification (LAMP) assay device comprising:
a heating chamber wherein the heating chamber comprises:
at least two internal heating elements;
a circuit of light-emitting elements positioned on one of a front wall or a rear wall of the heating chamber; and
a circuit of light sensors positioned opposite the circuit of light-emitting elements on one of the front wall or the rear wall of the heating chamber;
a removeable support rail wherein the heating chamber is configured to receive the removeable support rail configured to hold one or more samples when the removeable support rail is inserted into the heating chamber through a sample insertion opening; and
a real-time control system wherein the real-time control system is configured to control a temperature of the heating chamber during a stabilization cycle while the removeable support rail is outside the heating chamber by controlling current flow through the at least two internal heating elements fixed inside the heating chamber,
wherein, after the stabilization cycle, the real-time control system is configured to provide thermal control exclusively based on thermal inertia of the at least two internal heating elements of the heating chamber during a reaction mode based on a speed with which an environment inside the heating chamber gains or loses heat to an environment outside the heating chamber while the removeable support rail is inserted into the heating chamber,
wherein for each sample of the one or more samples that the removeable support rail is configured to hold, one of the light-emitting elements is configured to be positioned opposite one of the light sensors,
wherein one of the internal heating elements is positioned in a lower portion of the heating chamber, and another one of the internal heating elements is positioned in an upper portion of the heating chamber,
wherein the at least two internal heating elements are of a resistive type and are fixed inside the heating chamber, and
wherein the internal heating element positioned in the upper portion comprises a heating circuit with a first resistance value and the internal heating element positioned in the lower portion comprises a heating circuit with a second resistance value, the first resistance value being less than the second resistance value,
wherein the heating chamber comprises a temperature sensor positioned in an intermediate region of the heating chamber, and
wherein the real-time control system is configured to communicate with the at least two internal heating elements, the circuit of light-emitting elements, the circuit of light sensors, and the temperature sensor, and is configured to control the at least two internal heating element during a stabilization cycle while the removeable support rail is outside the heating chamber and during the reaction mode while the removeable support rail is inside the heating chamber.

* * * * *